United States Patent [19]

Safir

[11] 4,007,272
[45] Feb. 8, 1977

[54] SUBSTITUTED BENZODIAZEPIN-10-ONES IN TREATING PAIN AND DEPRESSION

[75] Inventor: Sidney Robert Safir, River Edge, N.J.

[73] Assignee: American Cyanamid Company, Stamford, Conn.

[22] Filed: Jan. 29, 1976

[21] Appl. No.: 653,404

Related U.S. Application Data

[62] Division of Ser. No. 552,023, Feb. 24, 1975, Pat. No. 3,953,430.

[52] U.S. Cl. .......................... 424/248.51; 424/244; 424/250; 424/267; 424/274; 424/275
[51] Int. Cl.[2] .............. A61K 31/33; A61K 31/445; A61K 31/495; A61K 31/535

[58] Field of Search .......... 424/275, 244, 263, 248, 424/250, 267

*Primary Examiner*—Stanley J. Friedman
*Attorney, Agent, or Firm*—Denis A. Polyn

[57] ABSTRACT

9-Aminoalkyl-4,9-dihydro-10H-thieno[3,4-b][1,5]benzodiazepin-10-ones having anti-depressant and analgesic activity and which are intermediates for other compounds having central nervous system activity.

1 Claim, No Drawings

SUBSTITUTED BENZODIAZEPIN-10-ONES IN TREATING PAIN AND DEPRESSION

This is a division, of application Ser. No. 552,023, filed Feb. 24, 1975, now U.S. Pat. No. 3,953,430.

DESCRIPTION OF THE INVENTION

This invention is concerned with compounds of the formula:

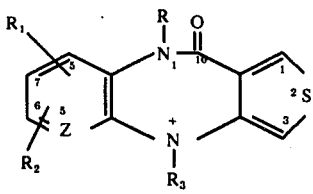

wherein Z is CH or N; $R_1$ and $R_2$ are the same or different and are selected from the group consisting of hydrogen, lower alkyl, lower alkoxy, halogen, nitro, trifluoromethyl, methylthio, methylsulfonyl and hydroxy; $R_3$ is hydrogen, lower alkyl or phenyl lower alkyl; R is hydrogen, diloweralkylaminoloweralkyl, piperidylloweralkyl, morpholinoloweralkyl, pyrrolidinoloweralkyl, or piperazinylloweralkyl and acid addition salts thereof, with the proviso that when Z is N, then $R_1$ and $R_2$ are hydrogen. The term lower in compounds containing lower alkyl or lower alkoxy substituents is intended to include those having from 1 to 4 carbon atoms. The term halogen includes chlorine, bromine, fluorine and iodine.

This invention also relates to compounds of the above formula wherein $R_3$ is hydrogen or lower alkyl, R is hydrogen and $R_1$, $R_2$ and Z are as described above, which compounds are useful as intermediates for the preparation of the compounds of my application Ser. No. 552,023, filed Feb. 24, 1975, now U.S. Pat. No. 3,953,430.

The compounds of the present invention may be prepared according to the following reaction sequence:

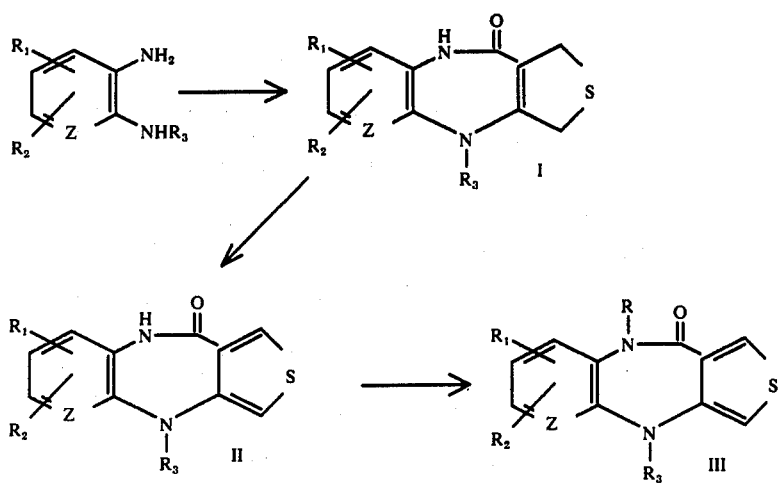

wherein R, $R_1$, $R_2$, $R_3$ and Z are as defined hereinabove.

An appropriately substituted 1,3,4,9-tetrahydro-10H-thieno[3,4-b][1,5]benzodiazepin-10-one (I) wherein Z is CH, $R_1$ and $R_2$ are hydrogen and $R_3$ is methyl is prepared by the reaction of N-methyl-o-phenylenediamine and methyl tetrahydro-4-oxo-3-thiophenecarboxylate at reflux temperature. The compound (I) is then fused with sulfur to produce the comparably substituted 4,9-dihydro-10H-thieno[3,4-b][1,5]benzodiazepin-10-one (II). The compound (II) is then reacted with an appropriately substituted diloweralkylaminoloweralkyl, piperazinylloweralkyl, phenylloweralkyl, pyrrolidinoloweralkyl, piperidylloweralkyl or morpholinoloweralkyl halide in a sodium hydride-mineral oil dispersion and an appropriate solvent such as dry dimethylformamide to produce the compounds (III) exemplified by Examples 4–13.

The compounds of Examples 14–17 may be prepared by the above procedure where (I) has the $R_3$ substituent altered to ethyl by employing N-ethyl-o-phenylenediamine. The compound (I) is then reacted with N-chlorosuccinimide in a suitable solvent to produce compound (II) where $R_3$ is ethyl. The compound (II) is then reacted as described above to produce the compounds exemplified by Examples 16 and 17.

To produce the compound of Example 20 an appropriately substituted 1,3,4,9-tetrahydro-10H-thieno[3,4-b][1,5]benzodiazepin-10-one (I) wherein Z is CH, and $R_1$, $R_2$ and $R_3$ are each methyl is prepared by the reaction of N-methyl-4,5-dimethyl-o-phenylenediamine and methyl tetrahydro-4-oxo-3-thiophenecarboxylate at reflux temperature. The compound (I) is then treated with N-chlorosuccinimide in a solvent such as dry pyridine to produce the comparably substituted compound (II). The compound (II) is then reacted as described above to produce the compound of Example 20.

The compound (I) where $R_1$ and $R_2$ are chloro, Z is CH and $R_3$ is methyl is prepared by the reaction of N-methyl-4,5-dichloro-o-phenylenediamine and methyl tetrahydro-4-oxo-3-thiophenecarboxylate at reflux temperature. This compound (I) is converted to the comparably substituted compound (II) by reaction with N-chlorosuccinimide. This compound (II) is then converted to the compound (III) exemplified by Example 23, by the procedure described above.

The appropriately substituted compound (I) where Z is CH, R, $R_1$ and $R_2$ are hydrogen is prepared by the reaction of methyl tetrahydro-4-oxo-3-thiophenecarboxylate and o-phenylenediamine in a solvent such as for example, toluene at reflux temperature. Compound (I) is converted to the comparably substituted compound (II) by treatment with N-bromosuccinimide in dimethylformamide at ambient temperature. Compound (II) is then converted to the comparably substituted compounds (III) of Examples 26, 27 and 28, by the above described procedure.

The compound (I) where Z is nitrogen, $R_1$ and $R_2$ are hydrogen and $R_3$ is methyl is prepared by the reaction of 2-methylamino-3-aminopyridine and methyl tetrahydro-4-oxo-3-thiophenecarboxylate in toluene at reflux temperature. Compound (I) is converted to the comparably substituted compound (II) by treatment with N-chlorosuccinimide in pyridine. Compound (II) is converted to the compounds (III) exemplified by Examples 31 and 32, by the above described procedure.

Compounds included within the scope of this invention, having anti-depressant or analgesic activity are, for example:

9-(3-Dimethylaminopropyl)-4,9-dihydro-4-methyl-10H-thieno[3,4-b][1,5]benzodiazepin-10-one
9-(2-Dimethylaminoethyl)-4,9-dihydro-4-methyl-10H-thieno[3,4-b][1,5]benzodiazepin-10-one
4,9-Dihydro-4-methyl-9-[2-(4-phenyl-1-piperazinyl)ethyl]-10H-thieno[3,4-b][1,5]benzodiazepin-10-one
5,10-Dihydro-5-(2-dimethylaminoethyl)-10-methyl-6H-pyrido[3,2-b]thieno[3,4-e][1,4]diazepin-6-one
9-(2-Diethylaminoethyl)-4,9-dihydro-4-methyl-10H-thieno[3,4-b][1,5]benzodiazepin-10-one
4,9-Dihydro-4-methyl-9-[2-(1-pyrrolidinyl)ethyl]-10H-thieno[3,4-b][1,5]benzodiazepin-10-one
9-(2-Dimethylaminoethyl)-4,9-dihydro-4-ethyl-10H-thieno[3,4-b][1,5]benzodiazepin-10-one
4,9-Dihydro-4-methyl-9-(2-morpholinoethyl)-10H-thieno[3,4-b][1,5-benzodiazepin-10-one
6,7-Dichloro-4,9-dihydro-9-(2-dimethylaminoethyl)-4-methyl-10H-thieno[3,4-b][1,5]benzodiazepin-10-one
4,9-Dihydro-4-methyl-9-(2-piperidinoethyl)-10H-thieno[3,4-b][1,5]benzodiazepin-10-one
9-(3-Dimethylaminopropyl)-4,9-dihydro-4-ethyl-10H-thieno[3,4-b][1,5]benzodiazepin-10-one
5,10-Dihydro-5-(3-dimethylaminopropyl)-10-methyl-6H-pyrido[3,2-b]thieno[3,4-e][1,4]diazepin-6-one
9-(2-Dimethylamino-1-methylethyl)-4,9-dihydro-4-methyl-10H-thieno[3,4-b][1,5]benzodiazepin-10-one
9-(2-Dimethylaminoethyl)-4,9-dihydro-4,6,7-trimethyl-10H-thieno[3,4-b][1,5]benzodiazepin-10-one
9-(3-Dimethylamino-2-methylpropyl)-4,9-dihydro-4-methyl-10H-thieno[3,4-b][1,5]benzodiazepin-10-one
9-(3-Diethylaminopropyl)-4,9-dihydro-4-methyl-10H-thieno[3,4-b][1,5]benzodiazepin-10-one
9-(4-Dimethylaminobutyl)-4,9-dihydro-4-methyl-10H-thieno[3,4-b][1,5]benzodiazepin-10-one Compounds included within the scope of this invention which have utility as intermediates for the preparation of the compounds of application Ser. No. 552,023, filed Feb. 24, 1975, now U.S. Pat. No. 3,953,430, include, for example:

4,9-Dihydro-10H-thieno[3,4-b][1,5]benzodiazepin-10-one
4,9-Dihydro-4-methyl-10H-thieno[3,4-b][1,5]benzodiazepin-10-one
4,9-Dihydro-4-ethyl-10H-thieno[3,4-b][1,5]benzodiazepin-10-one
5,10-Dihydro-10-methyl-6H-pyrido[3,2-b]thieno[3,4-e][1,4]diazepin-6-one
4,9-Dihydro-4,6,7-trimethyl-10H-thieno[3,4-b][1,5]benzodiazepin-10-one
6,7-Dichloro-4,9-dihydro-4-methyl-10H-thieno[3,4-b][1,5]benzodiazepin-10-one
7-Chloro-4,9-dihydro-10H-thieno[3,4-b][1,5]benzodiazepin-10-one
7-Chloro-4,9-dihydro-4-methyl-10H-thieno[3,4-b][1,5]benzodiazepin-10-one
6-Chloro-4,9-dihydro-10H-thieno[3,4-b][1,5]benzodiazepin-10-one
5-Chloro-4,9-dihydro-10H-thieno[3,4-b][1,5]benzodiazepin-10-one
5-Chloro-4,9-dihydro-4-methyl-10H-thieno[3,4-b][1,5]benzodiazepin-10-one
8-Chloro-4,9-dihydro-4-methyl-10H-thieno[3,4-b][1,5]benzodiazepin-10-one
8-Chloro-4,9-dihydro-10H-thieno[3,4-b][1,5]benzodiazepin-10-one
6-Methoxy-4,9-dihydro-10H-thieno[3,4-b][1,5]benzodiazepin-10-one
7-Methoxy-4,9-dihydro-10H-thieno[3,4-b][1,5]benzodiazepin-10-one
6-Trifluoromethyl-4,9-dihydro-10H-thieno[3,4-b][1,5]benzodiazepin-10-one
7-Trifluoromethyl-4,9-dihydro-10H-thieno[3,4-b][1,5]benzodiazepin-10-one
6-Fluoro-4,9-dihydro-10H-thieno[3,4-b][1,5]benzodiazepin-10-one
7-Fluoro-4,9-dihydro-4-methyl-10H-thieno[3,4-b][1,5]benzodiazepin-10-one
7-Fluoro-4,9-dihydro-10H-thieno[3,4-b][1,5]benzodiazepin-10-one
7-Hydroxy-4,9-dihydro-10H-thieno[3,4-b][1,5]benzodiazepin-10-one
6-Hydroxy-4,9-dihydro-10H-thieno[3,4-b][1,5]benzodiazepin-10-one
5-Hydroxy-4,9-dihydro-10H-thieno[3,4-b][1,5]benzodiazepin-10-one
7-Hydroxy-4,9-dihydro-4-methyl-10H-thieno[3,4-b][1,5]benzodiazepin-10-one
8-Hydroxy-4,9-dihydro-10H-thieno[3,4-b][1,5]benzodiazepin-10-one
7-Methylsulfonyl-4,9-dihydro-10H-thieno[3,4-b][1,5]benzodiazepin-10-one
7-Methyl-4,9-dihydro-4-methyl-10H-thieno[3,4-b][1,5]benzodiazepin-10-one
7-Methyl-4,9-dihydro-10H-thieno[3,4-b][1,5]benzodiazepin-10-one
7-Methylthio-4,9-dihydro-4-methyl-10H-thieno[3,4-b][1,5]benzodiazepin-10-one
7-Methylthio-4,9-dihydro-10H-thieno[3,4-b][1,5]benzodiazepin-10-one The compounds of this invention show anti-anxiety activity by their ability to protect warm-blooded animals from convulsions resulting from the administration of pentylenetetrazol. Graded dose levels of the test compounds are administered orally in a 2% starch vehicle, to groups of at least 5 rats. At the estimated time of peak effect, the rats are treated intravenously with pentylenetetrazol at a dose of 21 to 23 mg./kg. of body weight. This dose is estimated to cause clonic seizures in 99% of unprotected rats. The effective dose of the test compounds for protection of 50% of the animals ($MDD_{50}$) is calculated by the method of D. H. Finney in Statistical Methods in Biological Assay, Second Edition, Hofner Publishing Co., New York 456–457 (1964) or by the method of Litchfield, J. T. and Wilcoxon, F., J. Pharmacol. and Exp. Ther., 96, 99 (1949).

It has been reported [R. T. Hill and D. M. Tedeschi, "Animal Testing and Screening Procedures in Evaluating Psychotropic Drugs", in An Introduction to Psychopharmacology, Eds. R. R. Rech and K. E. Moore, Raven Press, New York, pp. 237–288 (1971)] that there is a high degree of correlation between anticonvulsant effects in rodents and anti-anxiety effects in higher warm-blooded animals. The results of this test on representative compounds of the present invention are summarized in Table I.

Table I

| Compound | Median Effective Dose (mg/kg) Orally |
| --- | --- |
| 4,9-Dihydro-9-(2-dimethyl-aminoethyl)-4-methyl-10H-thieno[3,4-b][1,5]benzo-diazepin-10-one | 200 |
| 4,9-Dihydro-4-methyl-9-(2-morpholinoethyl)-10H-thieno-[3,4-b][1,5]benzodiazepin-10-one | 200 |

The compounds of the present invention are active analgesics when measures by the "writhing syndrome" test for analgesic activity as described by Siegmund, et al., Proc. Soc. Exp. Bio. and Med., 95, 729 (1957), with modifications. This method is based upon the reduction of the number of writhes following the intraperitoneal injection of one mg./kg. of body weight of phenyl p-quinone in male Swiss albino mice weighing 18–25 gm. The syndrome is characterized by intermittent contractions of the abdomen, twisting and turning of the trunk, and extension of the hind legs beginning 3 to 5 minutes after injection of the phenyl p-quinone. The test compounds are administered orally at the indicated dose to groups of 2 mice each, 30 minutes before injection of the phenyl p-quinone. The total number of writhes exhibited by each group of mice is recorded for a 3 minute period commencing 15 minutes after injection of the phenyl p-quinone. A compound is considered active if it reduces the total number of writhes in 2 test mice from a control value of approximately 30 per pair to a value of 18 or less. Table II summarizes the results of this test on representative compounds of this invention.

The compounds of the present invention exhibit antidepressant activity when tested for inhibition of tetrabenazine depression in warm-blooded animals. Doses of 25 mg./kg. of body weight of the test compounds are administered intraperitoneally to 5 mice one hour before the administration of tetrabenazine hexamate at an intraperitoneal dose of 30 mg./kg. which is known to depress markedly the exploratory behavior of normal mice. Thirty minutes later the mice are tested for their exploratory behavior. Individual mice are placed in the center of a horizontal disc. Inhibition of the depression induced by tetrabenazine is considered present if the mice perform one or more of the following actions within 10 seconds after being placed on the disc:

1. Animals move to the edge of the disc and peer over the side.
2. Animals move 180° in place.
3. Animals display a head movement of 90° immediately followed by a head movement in the opposite direction of at least 45°.

Administration of the test compounds to additional groups of 5 mice is repeated, the numbers of individual animals showing an anti-depressant response (normal exploratory behavior) is recorded and the results are analyzed by the following scheme (statistically standardized; significant P = less than 0.05).

| | No. Active/ No. Tested | Result |
| --- | --- | --- |
| 1st Stage (5 animals) | 0/5 | Reject (ineffective anti-depressant) |
| | 1/5–3/5 | Continue to Stage 2 |
| | ≧ 4/5 | Accept (active anti-depressant) |
| 2nd Stage | 1/10 | Reject |
| | 2/10–3/10 | Continue to Stage 3 |
| | ≧ 4/10 | Accept |
| 3rd Stage | 4/15 | Reject |
| | ≧ 4/15 | Accept |

When a given test compound is accepted by this procedure at the designated dose level, the sequential procedure is then repeated at the same dose level to provide unequivocal confirmation of its acceptance as an active anti-depressant. The results from several dose levels (acceptance in at least two sequential test procedures) are then used to establish the Range of Active Table II

| Compound | Dose (mg/kg) | No. of Writhes Per Pair |
| --- | --- | --- |
| 4,9-Dihydro-9-(2-dimethylaminoethyl)-4-methyl-10H-thieno [3,4-b][1,5]benzodiazepin-10-one | 200 | 0, 0 |
| 4,9-Dihydro-9-(3-dimethylaminopropyl)-4-methyl-10H-thieno[3,4-b][1,5]benzodiazepin-10-one | 200 | 17, 18 |
| 9-(2-Diethylaminoethyl)-4-methyl-10H-thieno-[3,4-b][1,5]benzodiazepin-10-one | 100 | 11, 10 |
| 4,9-Dihydro-9-(2-dimethylamino-1-methylethyl)-4-methyl-10H-thieno [3,4-b][1,5]benzodiazepin-10-one | 200 | 0, 5 |
| 4,9-Dihydro-9-[2-(4-phenyl-1-piperazinyl)ethyl]-10H-thieno[3,4-b][1,5]benzodiazepin-10-one | 200 | 13, 16 |
| 4,9-Dihydro-4-methyl-9-(2-piperidinoethyl)-10H-thieno[3,4-b][1,5]benzodiazepin-10-one | 100 | 14, 0 |
| 4,9-Dihydro-9-(2-dimethylaminoethyl)-4-ethyl-10H-thieno[3,4-b][1,5]benzodiazepin-10-one | 200 | 12, 6 |
| 4,9-Dihydro-9-(2-dimethylaminoethyl)-4,6,7-tri-methyl-10H-thieno[3,4-b][1,5]benzodiazepin-10-one | 200 | 0, 0 |
| 6,7-Dichloro-4,9-dihydro-9-(2-dimethylaminoethyl)-4-methyl-10H-thieno[3,4-b][1,5]benzodiazepin-10-one | 200 | 0, 0 |
| 5,10-Dihydro-5-(2-dimethylaminoethyl)-10-methyl-6H-pyrido[3,2-b]thieno[3,4-e][1,4]diazepin-6-one | 200 | 2, 0 |

Doses. This method has been described in Greenblatt, E. N. and Osterberg, A. C. in Toxicology and Applied Pharmacology 7, 566–578 (1965). The results of these tests with representative compounds of this invention are summarized in Table III.

Table III

| Compound | Active Doses (mg/kg intraperitoneally) |
|---|---|
| 4,9-Dihydro-9-(2-dimethylaminoethyl)-4-methyl-10H-thieno[3,4-b][1,5]benzodiazepin-10-one | 6.25 |
| 4,9-Dihydro-9-(3-dimethylaminopropyl)-4-methyl-10H-thieno[3,4-b][1,5]benzodiazepin-10-one | 6.25 |
| 9-(2-Diethylaminoethyl)-4,9-dihydro-4-methyl-10H-thieno[3,4-b][1,5]benzodiazepin-10-one | 6.25 |
| 4,9-Dihydro-9-(2-dimethylamino-1-methylethyl)-4-methyl-10H-thieno[3,4-b][1,5]-benzodiazepin-10-one | 6.25 |
| 5,10-Dihydro-5-(3-dimethylaminopropyl)-10-methyl-6H-pyrido[3,2-b]thieno[3,4-e]-[1,4]diazepin-6-one | 12.5 |

The active components of this invention can be used in compositions such as tablets; the principal active ingredient is mixed with conventional tableting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating.

The liquid forms in which the novel compositions of the present invention may be incorporated for administration include suitably flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The dosage may vary from 1 mg. to 70 mg. per kg. of warm-blooded animal per day preferably in multiple doses. The daily dosage requirement may be from 50 mg. to 2000 mg. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

SPECIFIC DETAILS OF THE INVENTION

The following examples describe in detail the preparation of compounds of the present invention.

EXAMPLE 1

Preparation of 1,3,4,9-Tetrahydro-4-methyl-10H-thieno[3,4-b][1,5]benzodiazepin-10-one An aqueous solution of 1.2 g. of N-methyl-o-phenylenediamine is made alkaline with excess 1N sodium hydroxide solution and is extracted with toluene. To the dried toluene extracts (100 ml.) is added 0.8 g. of methyl tetrahydro-4-oxo-3-thiophenecarboxylate. The solution is heated under reflux for 3 hours during which 50 ml. of distillate is collected in a Dean-Stark trap. The toluene solution is concentrated to dryness and the residue is recrystallized from ethyl acetate to give yellow crystals, m.p. 196°–198° C.

EXAMPLE 2

Preparation of 4,9-Dihydro-4-methyl-10H-thieno[3,4-b][1,5]benzodiazepin-10-one

A mixture of 0.5 g. of 1,3,4,9-tetrahydro-4-methyl-10H-thieno[3,4-b][1,5]benzodiazepin-10-one and 0.5 g. of sulfur is fused at 160° C. ± 5 for 1 hour. The fusion mixture is slurried with chloroform and filtered. The filtrate is chromatographed on silica gel with benzene:methanol 9:1 to give a solid, which is recrystallized from methanol-water to give a tan solid, m.p. 224°–225° C. (dec.).

EXAMPLE 3

Alternative Preparation of 4,9-Dihydro-4-methyl-10H-thieno[3,4-b][1,5]benzodiazepin-10-one To a suspension of 3.8 g. of 1,3,4,9-tetrahydro-4-methyl-10H-thieno[3,4-b][1,5]benzodiazepin-10-one in 15 ml. of dry pyridine is added, in portions, a total of 2.18 g. of N-chlorosuccinimide. The resulting solution is heated on a steam bath for 15 minutes, cooled and diluted with water. The solid is collected and recrystallized from methanol, to give a tan solid, m.p. 224°–225° C. (dec.).

EXAMPLE 4

Preparation of 4,9-Dihydro-9-(2-dimethylaminoethyl)-4-methyl-10H-thieno[3,4-b][1,5]benzodiazepin-10-one A mixture of 0.4 g. of 55% sodium hydride-mineral oil dispersion 0.5 g. of 2-dimethylaminoethylchloride hydrochloride and 25 ml. of dry dimethylformamide is stirred at room temperature for 0.5 hours. To the mixture is added 0.4 g. of 4,9-dihydro-4-methyl-10H-thieno[3,4-b][1,5]benzodiazepin-10-one and stirring at room temperature is continued for 18 hours. The reaction mixture is cooled, quenched with water, acidified, decolorized and filtered. The filtrate is made alkaline and extracted with chloroform. The dried chloroform extracts are concentrated to give a solid which is recrystallized from chloroform-hexane to give off-white crystals, m.p. 147°–149° C.

EXAMPLE 5

Preparation of
4,9-Dihydro-9-(3-dimethylaminopropyl)-4-methyl-10H-thieno[3,4-b][1,5]benzodiazepin-10-one A mixture of 0.3 g. of 55% sodium hydride-mineral oil dispersion and 0.35 g. of 4,9-dihydro-4-methyl-10H-thieno-[3,4-b][1,5]benzodiazepin-10-one in 25 ml. of dry dimethylformamide is stirred at room temperature for 0.5 hours. To the mixture is added 0.45 g. of dimethylaminopropyl chloride and stirring at room temperature is continued for 18 hours. The reaction mixture is cooled, quenched with water, acidified, decolorized and filtered. The filtrate is made alkaline and extracted with chloroform. The dried chloroform extracts are concentrated under reduced pressure to give an oil which is crystallized by dissolving in boiling hexane and a minimal volume of ethyl acetate and cooling to give off-white crystals, m.p. 52°–56° C.

EXAMPLE 6

Preparation of 9-c
2-Diethylaminoethyl)-4,9-dihydro-4-methyl-10H-thieno[3,4-b][1,5]benzodiazepin-10-one A mixture of 0.31 g. of 55% sodium hydride-mineral oil dispersion and 0.60 g. of diethylaminoethylchloride hydrochloride in 25 ml. of dry dimethylformamide is stirred at room temperature for 0.5 hours. To the mixture is added 0.4 g. of 4,9-dihydro-4-methyl- 10H-thieno[3,4-b][1,5]benzodiazepin-10-one and stirring is continued for 18 hours. The reaction mixture is cooled, quenched with water and extracted with chloroform. The chloroform extracts are concentrated under reduced pressure to an oil, which is chromatographed on silica gel preparative thin layer chromatographic (tlc) plates using 10:1 benzene:methanol as eluent. The oily product is crystallized from hexane to give white crystals, m.p. 92°–93° C.

EXAMPLE 7

Preparation of
9-(2-Dimethylamino-1-methylethyl)-4,9-dihydro-4-methyl-10H-thieno[3,4-b][1,5]benzodiazepin-10-one, hydrochloride A mixture of 0.47 g. of 55% sodium hydride-mineral oil dispersion and 0.83 g. of 2-dimethylamino-1-methylethylchloride hydrochloride in 30 ml. of dry dimethylformamide is stirred at room temperature for 0.5 hours. To the mixture is added 0.6 g. of 4,9-dihydro-4-methyl-10H-thieno[3,4-b][1,5]-benzodiazepin-10-one and stirring is continued for 18 hours. The reaction mixture is cooled, quenched with water and extracted with chloroform. The dried chloroform extracts are concentrated to an oil which is chromatographed on silica gel preparative thin layer chromatographic (tlc) plates using 10:1 benzene:methanol to give a yellow oil. The oil is dissolved in ethanol and treated with anhydrous hydrogen chloride followed by dilution with ether to give a solid, which is recrystallized from ethanol to give white crystals, m.p. 280°–282° C. (dec.).

EXAMPLE 8

Preparation of
9-(3-Dimethylamino-2-methylpropyl)-4,9-dihydro-4-methyl-10H-thieno[3,4-b][1,5]benzodiazepin-10-one, hydrochloride A mixture of 0.47 g. of 55% sodium hydride-mineral oil dispersion and 0.91 g. of 3-dimethylamino-2-methylpropylchloride hydrochloride in 35 ml. of dry dimethylformamide is stirred at room temperature for 0.5 hours. To the mixture is added 0.6 g. of 4,9-dihydro-4-methyl-10H-thieno[3,4-b][1,5]-benzodiazepin-10-one and stirring is continued for 18 hours. The reaction mixture is cooled, quenched with water and extracted with chloroform. The dried chloroform extracts are concentrated to an oil, which is chromatographed on silica gel preparative thin layer chromatographic (tlc) plates with 10:1 benzene:methanol to give an oil. An ethanolic solution of the oil is treated with anhydrous hydrogen chloride and diluted with ether to give a white solid, m.p. 231°–233° C. (dec.).

EXAMPLE 9

Preparation of
4,9-Dihydro-4-methyl-9-[2-(4-phenyl-1-piperazinyl)ethyl]-10H-thieno[3,4-b][1,5]benzodiazepin-10-one, dihydrochloride A mixture of 0.13 g. of 55% sodium hydride-mineral oil dispersion and 0.5 g. of 4,9-dihydro-4-methyl-10H-thieno-[3,4-b][1,5]benzodiazepin-10-one in 25 ml. of dry dimethylformamide is stirred at room temperature for 0.5 hours. To the mixture is added 0.8 g. of N-(2-bromoethyl)-N'-phenylpiperazine and stirring is continued for 18 hours. The reaction mixture is cooled, quenched with water and extracted with chloroform. The dried chloroform extracts are concentrated to a brown oil, which is purified by preparative thin layer chromatography (tlc) on silica gel with 2:1 benzene:ethyl acetate as eluent. The oily product is converted to the dihydrochloride salt and recrystallized from ethanol-ether to give a white solid, m.p. 180°–183° C. (dec.).

EXAMPLE 10

Preparation of
4,9-Dihydro-4-methyl-9-[2-(1-pyrrolidinyl)ethyl]-10H-thieno[3,4-b][1,5]benzodiazepin-10-one A mixture of 0.31 g. of 55% sodium hydride-mineral oil dispersion and 0.60 g. of N-(2-chloroethyl)pyrrolidine hydrochloride in 25 ml. of dry dimethylformamide is stirred at room temperature for 0.5 hours. To the mixture is added 0.40 g. of 4,9-dihydro-4-methyl-10H-thieno[3,4-b][1,5]benzodiazepin-10-one and stirring is continued for 18 hours. The reaction mixture is cooled, quenched with water, and extracted with chloroform. The dried chloroform extracts are concentrated to an oil which crystallizes on trituration with ether. Recrystallization from ethyl acetate-hexane gives white crystals, m.p. 139°–141° C.

EXAMPLE 11

Preparation of
4,9-Dihydro-4-methyl-9-(2-piperidinoethyl)-10H-thieno[3,4-b][1,5]benzodiazepin-10-one A mixture of 0.31 g. of 55% sodium hydride-mineral oil dispersion and 0.65 g. of N-(2-chloroethyl)piperidine hydrochloride in 25 ml. of dry dimethylformamide is stirred at room temperature for 0.5 hours. To the mixture is added 0.40 g. of 4,9-dihydro-4-methyl-10H-thieno[3,4-b][1,5]benzodiazepin-10-one and stirring is continued for 18 hours. The reaction mixture is cooled, quenched with water and extracted with chloroform. The dried chloroform extracts are concentrated to an oil which is purified by preparative thin layer chromatography (tlc) on silica gel with 10:1 benzene:methanol as eluent. The oil obtained is crystallized from hexane to give white crystals, m.p. 84°–88° C.

EXAMPLE 12

Preparation of 4,9-Dihdryo-4-methyl-9-(2-morpholinoethyl)-10H-thieno[3,4-b][1,5]benzodiazepin-10-one A mixture of 0.31 g. of 55% sodium hydride-mineral oil dispersion and 0.65 g. of N-(2-chloroethyl)morpholine hydrochloride in 25 ml. of dry dimethylformamide is stirred at room temperature for 0.5 hours. To the mixture is added 0.40 g. of 4,9-dihydro-4-methyl-10H-thieno[3,4-b][1,5]benzodiazepin-10-one and stirring is continued for 18 hours. The reaction mixture is cooled, quenched with water and extracted with chloroform. The dried chloroform extracts are concentrated to dryness and the solid residue is recrystallized from ethyl acetate-hexane to give white crystals, m.p. 109°–111° C.

EXAMPLE 13

Preparation of 9-Benzyl-4,9-dihydro-4-methyl-10H-thieno[3,4-b]-[1,5]benzodiazepin-10-one A mixture of 0.35 g. of 4,9-dihydro-4-methyl-10H-thieno[3,4-b][1,5]benzodiazepin-10-one, 65 mg. of 57% sodium hydride-mineral oil dispersion and 0.3 ml. of benzylbromide in 10 ml. of dimethylformamide is stirred at room temperature for 3 hours, quenched by dropwise addition of water, diluted with 100 ml. of water and extracted several times with chloroform. The chloroform solution is dried over magnesium sulfate and concentrated under reduced pressure to give a yellow oil which is chromatographed on silica gel with benzene-methanol (19:1) to give an oil which crystallizes on trituration with acetonitrile. Recrystallization from methanol-water gives off-white crystals, m.p. 137°–138.5° C.

EXAMPLE 14

Preparation of 4-Ethyl-1,3,4,9-tetrahydro-10H-thieno[3,4-b]-[1,5]benzodiazepin-10-one An aqueous suspension of 4.3 g. of N-ethyl-o-phenylenediamine hdyrochloride is made alkaline with excess sodium hydroxide solution and is extracted with toluene. To the dried toluene extracts (200 ml.) is added 2.4 g. of methyl tetrahydro-4-oxo-3-thiophenecarboxylate. The solution is heated under reflux for 3 hours, during which 100 ml. of distillate is collected in a Dean-Stark trap. The toluene solution is concentrated to dryness and the residue is recrystallized from ethyl acetate to give yellow crystals. m.p. 195°–197° C.

EXAMPLE 15

Preparation of 4,9-Dihydro-4-ethyl-10H-thieno[3,4-b][1,5]benzodiazepin-10-one

To a suspension of 0.246 g. of 4-ethyl-1,3,4,9-tetrahydro-10H-thieno[3,4-b][1,5]benzodiazepin-10-one in 2 ml. of dry pyridine is added in portions a total of 0.133 g. of N-chlorosuccinimide. The resulting solution is heated on a steam bath for 15 minutes, cooled and diluted with water. The solid is collected and recrystallized from methanol-water to give off-white crystals, m.p. 201°–202° C.

EXAMPLE 16

Preparation of 9-(2-Dimethylaminoethyl)-4,9-dihydro-4-ethyl-10H-thieno[3,4-b][1,5]benzodiazepin-10-one A mixture of 0.31 g. of 55% sodium hydride-mineral oil dispersion and 0.50 g. of dimethylaminoethylchloride hydrochloride in 25 ml. of dry dimethylformamide is stirred at room temperature for 0.5 hours. To the mixture is added 0.43 g. of 4,9-dihydro-4-ethyl-10H-thieno[3,4-b][1,5]benzodiazepin-10-one and stirring is continued for 18 hours. The reaction mixture is cooled, quenched with water, and extracted with chloroform. The dried chloroform extracts are concentrated to an oil, which is purified by preparative thin layer chromatography on silica gel with 10:1 benzene:methanol as eluent. The oily solid thus obtained is recrystallized from hexane to give white crystals, m.p. 75°–77° C.

EXAMPLE 17

Preparation of 9-(3-Dimethylaminopropyl)-4,9-dihydro-4-ethyl-10H-thieno[3,4-b][1,5]benzodiazepin-10-one, perchlorate A mixture of 0.46 g. of 55% sodium hydride-mineral oil dispersion and 0.49 g. of 4,9-dihydro-4-ethyl-10H-thieno-[3,4-b][1,5]benzodiazepin-10-one in 25 ml. of dry dimethylformamide is stirred at room temperature for 0.5 hours. To the mixture is added 0.6 ml. of dimethylaminopropylchloride and stirring is continued for 18 hours. The reaction mixture is cooled, quenched with water and extracted with chlorofrom. The dried chloroform extracts are concentrated to an oil which is chromatographed on preparative silica gel thin layer chromatographic plates with 10:1 benzene:methanol as eluent. The oil obtained after chromatography is dissolved in ethanol, treated with perchloric acid and diluted with water to give a white solid. Recrystallization from water gives white crystals, m.p. 154°–156° C.

EXAMPLE 18

Preparation of 1,3,4,9-Tetrahydro-4,6,7-trimethyl-10H-thieno[3,4-b][1,5]benzodiazepin-10-one An aqueous suspension of 4.7 g. of N-methyl-4,5-dimethyl-o-phenylenediamine dihydrochloride is made alkaline with sodium hydroxide solution and is extracted with toluene. To the dried toluene extracts (400 ml.) is added 2.25 g. of methyl tetrahydro-4-oxo-3-thiophenecarboxylate. The solution is heated under reflux for 3 hours, during which 250 ml. of distillate is collected in a Dean-Stark trap. The solution is cooled and the solid which separates is collected and recrystallized from ethyl acetate to give yellow crystals, m.p. 250°–252° C. (dec.).

EXAMPLE 19

Preparation of 4,9-Dihydro-4,6,7-trimethyl-10H-thieno[3,4-b]-[1,5]benzodiazepin-10-one To a suspension of 0.40 g. of 1,3,4,9-tetrahydro-4,6,7-trimethyl-10H-thieno[3,4-b][1,5]benzodiazepin-10-one in 3 ml. of dry pyridine is added, in portions, a total of 0.21 g. of N-chlorosuccinimide. The resulting solution is heated on a steam bath for 15 minutes, cooled and diluted with water. The solid which separates is collected and recrystallized from methanol to give yellow crystals, m.p. 260°–262° C.

EXAMPLE 20

Preparation of 9-(2-Dimethylaminoethyl)-4,9-dihydro-4,6,7-trimethyl-10H-thieno[3,4-b][1,5]benzodiazepin-10-one A mixture of 0.36 g. of 55% sodium hydride-mineral oil dispersion and 0.58 g. of dimethylaminoethylchloride hydrochloride in 25 ml. of dry dimethylformamide is stirred at room temperature for 0.5 hours. To the mixture is added 0.52 g. of 4,9-dihydro-4,6,7-trimethyl-10H-thieno[3,4-b][1,5]benzodiazepin-10-one and stirring is continued for 18 hours. The reaction mixture is cooled, quenched with water, and extracted with chloroform. The dried chloroform extracts are concentrated to an oil, which is purified by preparative thin layer chromatography (tlc) on silica gel with 10:1 benzene:methanol as eluent. The oil obtained is crystallized from hexane to give white crystals, m.p. 119°–120° C.

EXAMPLE 21

Preparation of 6,7-Dichloro-1,3,4,9-tetrahydro-4-methyl-10H-thieno[3,4-b][1,5]benzodiazepin-10-one A solution of 2.7 g. of N-methyl-4,5-dichloro-o-phenylenediamine and 1.85 g. of methyl tetrahydro-4-oxo-3-thiophenecarboxylate in 150 ml. of toluene is heated under reflux for 3 hours during which 100 ml. of distillate is collected in a Dean-Stark trap. The solution is cooled and the solid which separates is recrystallized from ethyl acetate to give yellow crystals, m.p. 281°–283° C.

EXAMPLE 22

Preparation of 6,7-Dichloro-4,9-dihydro-4-methyl-10H-thieno[3,4-b][1,5]benzodiazepin-10-one To a suspension of 0.40 g. of 6,7-dichloro-1,3,4,9-tetrahydro-4-methyl-10H-thieno[3,4-b][1,5]benzodiazepin-10-one in 2.7 ml. of dry pyridine is added, in portions. a total of 0.18 g. of N-chlorosuccinimide. The resulting solution is heated on a steam bath for 15 minutes, cooled and diluted with water. The solid which separates is collected and recrystallized from methanol-water to give off-white crystals, m.p. 270°–272° C. (dec.).

EXAMPLE 23

Preparation of 6,7-Dichloro-9-(2-dimethylaminoethyl)-4-methyl-10H-thieno[3,4-b][1,5]benzodiazepin-10-one, perchlorate A mixture of 0.27 g. of 55% sodium hydride-mineral oil dispersion and 0.43 g. of dimethylaminoethylchloride hydrochloride in 25 ml. of dry dimethylformamide is stirred at room temperature for 0.5 hours. To the mixture is added 0.45 g. of 6,7-dichloro-4-methyl-10H-thieno[3,4-b][1,5]benzodiazepin-10-one and stirring is continued for 18 hours. The mixture is cooled, quenched with water and extracted with chloroform. The dried chloroform extracts are concentrated to an oil, which is purified by preparative thin layer chromatography (tlc) on silica gel with 10:1 benzene:methanol as eluent. The oil obtained is treated with aqueous perchloric acid to give a solid, which is recrystallized from isopropyl alcohol to give yellow crystals, m.p. 223°–225° C. (dec.).

EXAMPLE 24

Preparation of 1,3,4,9-Tetrahydro-10H-thieno[3,4-b][1,5]benzodiazepin-10-one A solution of 0.4 g. of methyl tetrahydro-4-oxo-3-thiophenecarboxylate and 0.27 g. of o-phenylenediamine in 35 ml. of toluene is heated under reflux for 2.5 hours during which 15 ml. of distillate is collected in a Dean-Stark trap. The solution is cooled and the precipitate is collected. Recrystallization from dimethylformamide-water gives a yellow solid, m.p. 216°–218° C.

In a similar fashion 4-fluoro-o-phenylenediamine is condensed with methyl tetrahydro-4-oxo-3-thiophenecarboxylate to give a mixture of 7-fluoro- and 6-fluoro-1,3,4,9-tetrahydro-10H-thieno[3,4-b][1,5]benzodiazepin-10-one.

Employing the same general procedure the following starting materials produce their corresponding mixture of products:

| | | |
|---|---|---|
| 4-methoxy-o-phenylenediamine | ⟶ | 7-methoxy- and 6-methoxy-1,3,4,9-tetrahydro-10H-thieno[3,4-b][1,5]benzodiazepin-10-one |
| 4-hydroxy-o-phenylenediamine | ⟶ | 7-hydroxy- and 6-hydroxy-1,3,4,9-tetrahydro-10H-thieno[3,4-b][1,5]benzodiazepin-10-one |
| 4-trifluoromethyl-o-phenylenediamine | ⟶ | 7-trifluoromethyl- and 6-trifluoromethyl-1,3,4,9-tetra- |

-continued

| | | |
|---|---|---|
| | | hydro-10H-thieno[3,4-b][1,5]-benzodiazepin-10-one |
| 3-fluoro-o-phenylenediamine | ⟶ | 5-fluoro- and 8-fluoro-1,3,-4,9-tetrahydro-10H-thieno-[3,4-b][1,5]benzodiazepin-10-one |
| 4-nitro-o-phenylenediamine | ⟶ | 7-nitro- and 6-nitro-1,3,4,-9-tetrahydro-10H-thieno-[3,4-b][1,5]benzodiazepin-10-one |
| 4-methylthio-o-phenylenediamine | ⟶ | 7-methylthio- and 6-methyl-thio-1,3,4,9-tetrahydro-10H-thieno[3,4-b][1,5]-benzodiazepin-10-one |
| 4-methylsulfonyl-o-phenylene | ⟶ | 7-methylsulfonyl- and 6-methylsulfonyl-1,3,4,9-tetrahydro-10H-thieno-[3,4-b][1,5]benzodiazepin-10-one |

EXAMPLE 25

Preparation of 4,9-Dihydro-10H-thieno[3,4-b][1,5]benzodiazepin-10-one

A solution of 1.1 g. of 1,3,4,9-tetrahydro-10H-thieno[3,4-b][1,5]benzodiazepin-10-one and 0.9 g. of N-bromosuccinimide in 30 ml. of dimethylformamide is stirred for 1 hour at room temperature, diluted with 200 ml. of water and cooled. The precipitate is collected and recrystallized from methanol-water to give tan crystals, m.p. 218°–220° C. (dec.).

In a similar fashion the mixture of 7-fluoro- and 6-fluoro-1,3,4,9-tetrahydro-10H-thieno[3,4-b][1,5]benzodiazepin-10-one is treated with N-bromosuccinimide to give 7-fluoro- and 6-fluoro-4,9-dihydro-10H-thieno[3,4-b][1,5]benzodiazepin-10-one.

Employing the same general procedure the following starting materials produce their corresponding mixture of products:

| | | |
|---|---|---|
| 7-methoxy- and 6-methoxy-1,3,4,9-tetrahydro-10H-thieno[3,4-b][1,5]benzo-diazepin-10-one | ⟶ | 7-methoxy- and 6-methoxy-4,9-dihydro-10H-thieno-[3,4-b][1,5]benzodiazepin-10-one |
| 7-hydroxy- and 6-hydroxy-1,3,4,9-tetrahydro-10H-thieno[3,4-b][1,5]benzo-diazepin-10-one | ⟶ | 7-hydroxy- and 6-hydroxy-4,9-dihydro-10H-thieno-[3,4-b][1,5]benzodiazepin-10-one |
| 7-trifluoromethyl- and 6-trifluoromethyl-1,3,4,9-tetrahydro-10H-thieno[3,4-b][1,5]benzodiazepin-10-one | ⟶ | 7-trifluoromethyl- and 6-trifluoromethyl-4,9-dihy-dro-10H-thieno[3,4-b][1,5]benzodiazepin-10-one |
| 5-fluoro- and 8-fluoro-1,3,4,9-tetrahydro-10H-thieno[3,4-b][1,5]benzo-diazepin-10-one | ⟶ | 5-fluoro- and 8-fluoro-4,9-dihydro-10H-thieno[3,4-b]-[1,5]benzodiazepin-10-one |
| 7-nitro- and 6-nitro-1,3,4,9-tetrahydro-10H-thieno[3,4-b][1,5]benzo-diazepin-10-one | ⟶ | 7-nitro- and 6-nitro-4,9-dihydro-10H-thieno[3,4-b]-[1,5]benzodiazepin-10-one |
| 7-methylthio- and 6-methyl-thio-1,3,4,9-tetrahydro-10H-thieno[3,4-b][1,5]benzo-diazepin-10-one | ⟶ | 7-methylthio- and 6-methyl-thio-4,9-dihydro-10H-thieno-[3,4-b][1,5]benzodiazepin-10-one |
| 7-methylsulfonyl- and 6-methylsulfonyl-1,3,4,9-tetrahydro-10H-thieno-[3,4-b][1,5]benzodiazepin-10-one | ⟶ | 7-methylsulfonyl- and 6-methylsulfonyl-4,9-dihydro-10H-thieno[3,4-b][1,5]-benzodiazepin-10-one |

EXAMPLE 26

Preparation of 4,9-Dihydro-9-methyl-10H-thieno[3,4-b][1,5]benzodiazepin-10-one

To a stirred mixture of 0.84 g. of 4,9-dihydro-10H-thieno[3,4-b][1,5]benzodiazepin-10-one and 0.18 g. of 55% sodium hydride-mineral oil dispersion in 25 ml. of dimethylformamide is added 0.3 ml. of methyl iodide. The reaction mixture is stirred for 2.5 hours, cooled, diluted with water and filtered. The solid product is recrystallized from methanol-water to give pale yellow crystals, m.p. 195°–198° C.

EXAMPLE 27

Preparation of 4,9-Dihydro-4-(2-dimethylaminoethyl)-9-methyl-10H-thieno[3,4-b][1,5]benzodiazepin-10-one A mixture of 0.72 g. of 55% sodium hydride-mineral oil dispersion and 0.60 g. of dimethylaminoethylchloride hydrochloride in 25 ml. of dimethylsulfoxide is stirred at room temperature for 0.5 hours. To the mixture is added 0.46 g. of 4,9-dihydro-9-methyl-10H-thieno[3,4-b][1,5]benzodiazepin-10-one and stirring is continued for 3 hours. The reaction mixture is quenched by dropwise addition of water, diluted with about 200 ml. of water, acidified, filtered, made alkaline with 5N sodium hydroxide and extracted several times with chloroform. The chloroform extracts are dried over magnesium sulfate and concentrated under reduced pressure to give an amber oil. The oil is dissolved in a minimal volume of ethanolic hydrogen chloride solution and diluted with ether to give an oily semi-solid which slowly crystallizes. Recrystallization from ethanol-ether gives tan crystals, m.p. 245°–248° C. (dec.).

EXAMPLE 28

Preparation of 4-Benzyl-4,9-dihydro-9-methyl-10H-thieno[3,4-b][1,5]benzodiazepin-10-one To a stirred solution of 0.18 g. of 57% sodium hydride-mineral oil dispersion in 25 ml. of dimethylformamide is added 0.92 g. of 4,9-dihydro-9-methyl-10H-thieno[3,4-b][1,5]-benzodiazepin-10-one and 0.8 ml. of benzyl bromide. The mixture is stirred at room temperature for 3.5 hours, quenched by dropwise addition of water, diluted with 200 ml. of water and extracted several times with chloroform. The chloroform extracts are dried over magnesium sulfate and concentrated under reduced pressure to give an amber oil, which crystallizes on trituration with methanol. Recrystallization from aqueous methanol and then from ethyl acetate gives off-white crystals, m.p. 151.5°–153° C.

EXAMPLE 29

Preparation of 5,7,9,10-Tetrahydro-10-methyl-6H-pyrido[3,2-b]thieno[3,4-e][1,4]diazepin-6-one A solution of 3.4 g. of 2-methylamino-3-aminopyridine and 2.9 g. of methyl tetrahydro-4-oxo-3-thiophene carboxylate in 200 ml. of toluene is heated under reflux for 3 hours, during which 100 ml. of distillate is collected in a Dean-Stark trap. The solution is concentrated under reduced pressure and the solid residue is recrystallized from ethyl acetate to give pale yellow crystals, m.p. 240°–241° C.

EXAMPLE 30

Preparation of 5,10-Dihydro-10-methyl-6H-pyrido[3,2-b]thieno[3,4-e][1,4]diazepin-10-one To a suspension of 0.6 g. of 5,7,9,10-tetrahydro-10-methyl-6H-pyrido[3,2-b]thieno[3,4-e][1,4]diazepin-6-one in 5 ml. of dry pyridine is added, in portions, 0.34 g. of N-chlorosuccinimide. The resulting solution is heated on a steam bath for 15 minutes, cooled and diluted with water. The solid which separates is collected and recrystallized from aqueous methanol to give off-white crystals, m.p. 240°–241° C.

EXAMPLE 31

Preparation of 5,10-Dihydro-5-(2-dimethylaminoethyl)-10-methyl-6H-pyrido[3,2-b]thieno[3,4-e][1,4]diazepin-6-one A mixture of 0.20 g. of 55% sodium hydride-mineral oil dispersion and 0.3 g. of dimethylaminoethylchloride hydrochloride in 12 ml. of dry dimethylformamide is stirred at room temperature for 0.5 hours. To the mixture is added 0.23 g. of 5,10-dihydro-10-methyl-6H-pyrido[3,2-b]thieno[3,4-e][1,4]diazepin-6-one and stirring is continued for 18 hours. The reaction mixture is cooled, quenched with water and extracted with chloroform. The dried chloroform extracts are concentrated to give an amber oil, which is crystallized from hexane to give an off-white solid, m.p. 129°–130° C.

EXAMPLE 32

Preparation of 5,10-Dihydro-5-(3-dimethylaminopropyl)-10-methyl-6H-pyrido[3,2-b]thieno[3,4-e][1,4]diazepin-6-one A mixture of 0.69 g. of 55% sodium hydride-mineral oil dispersion and 0.9 ml. of dimethylaminopropylchloride in 30 ml. of dry dimethylformamide is stirred at room temperature for 0.5 hours. To the mixture is added 0.70 g. of 5,10-dihydro-10-methyl-6H-pyrido[3,2-b]thieno[3,4-e][1,4]diazepin-6-one and stirring is continued for 18 hours. The reaction mixture is cooled, quenched with water and extracted with chloroform. The dried chloroform extracts are concentrated to an amber oil, which is purified by preparative thin layer chromatography (tlc) on silica gel with 10:1 benzene:methanol as eluent to give a semi-solid. The perchlorate salt is prepared by standard procedures and is recrystallized from water to give a white solid, m.p. 263°–265° C. (dec.).

EXAMPLE 33

Preparation of 6-Chloro-4,9-dihydro-10H-thieno[3,4-b][1,5]benzodiazepin-10-one To a solution of 1.6 g. of a mixture of 7-chloro- and 6-chloro-1,3,4,9-tetrahydro-10H-thieno[3,4-b][1,5]benzodiazepin-10-one (prepared by the condensation of 4-chloro-o-phenylenediamine with methyl tetrahydro-4-oxo-3-thiophenecarboxylate in toluene at reflux temperature) in 12 ml. of pyridine, is added, portionwise, 0.85 g. of N-chlorosuccinimide. A 3 ml. portion of pyridine is added and the mixture is heated on a steam bath for 15–20 minutes. The mixture is cooled and diluted with water resulting in the formation of golden crystals which are collected by filtration. These are recrystallized from methanol yielding 0.39 g., m.p. 279°–281° C.

The filtrate from the water addition is processed as described in Example 34.

EXAMPLE 34

Preparation of 7-Chloro-4,9-dihydro-10H-thieno[3,4-b][1,5]benzodiazepin-10-one The aqueous filtrate, prepared as described in Example 33, is diluted further with water resulting in the formation of a yellow solid. This solid is recrystallized from aqueous methanol yielding 0.4 g., m.p. 197°–198° C.

EXAMPLE 35

Preparation of 7-Chloro-4,9-dihydro-4-methyl-10H-thieno[3,4-b][1,5]benzodiazepin-10-one A 532 mg. portion of 7-chloro-1,3,4,9-tetrahydro-4-methyl-10H-thieno[3,4-b][1,5]benzodiazepin-10-one (prepared by the reaction of 4-chloro-2-amino-N-methylaniline and 3-keto-4-carbomethoxy tetrahydro thiophene at reflux temperature in toluene) is suspended in 4 ml. of pyridine. A 276 mg. portion of N-chlorosuccinimide is added in portions while rinsing with 1 ml. of pyridine. The mixture is heated on a steam bath for 15–20 minutes, cooled and diluted with water yielding a brown solid which is recrystallized twice from methanol yielding 0.25 g., m.p. 244°–246° C.

I claim:

1. A method for the treatment of pain and depression in a warm-blooded animal which comprises administering to said animal a pharmaceutical carrier and an analgesic and antidepressant amount of a compound of the formula:

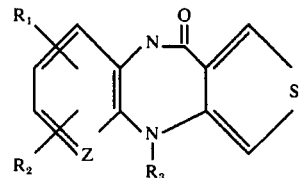

wherein Z is selected from the group CH and N; $R_1$ and $R_2$ are the same or different and are selected from the group consisting of hydrogen, lower alkyl, lower alkoxy, halogen, nitro, trifluoromethyl, methylthio, methylsulfonyl and hydroxy; $R_3$ is selected from the group consisting of hydrogen, lower alkyl and phenylloweralkyl and R is selected from the group comprising hydrogen, diloweralkylaminoloweralkyl, piperidylloweralkyl, morpholinoloweralkyl, pyrrolidinoloweralkyl and piperazinylloweralkyl and acid addition salts thereof, with the proviso that when Z is N, then $R_1$ and $R_2$ are hydrogen.

* * * * *